United States Patent

Cuschieri et al.

[11] Patent Number: 5,908,436
[45] Date of Patent: Jun. 1, 1999

[54] VUMEDICAL HANDLING DEVICE IN PARTICULAR FOR ENDOSCOPIC APPLICATIONS

[75] Inventors: Alfred Cuschieri, St. Andrews, ; Tim Frank, Newport-On-Tay, both of United Kingdom

[73] Assignee: Karl Storz GmbH & Co., Germany

[21] Appl. No.: 08/864,567

[22] Filed: May 28, 1997

[30] Foreign Application Priority Data

Dec. 18, 1996 [DE] Germany ............................ 196 52 792

[51] Int. Cl.⁶ .................................................. A61B 17/28
[52] U.S. Cl. ............................. 606/205; 606/1; 606/119; 606/139; 606/142; 606/144; 606/143; 606/167; 606/174; 606/205; 606/206; 606/207; 606/208
[58] Field of Search ................................. 606/1, 119, 139, 606/142, 143, 144, 167, 174, 205, 206, 207, 208

[56] References Cited

U.S. PATENT DOCUMENTS

| | | | |
|---|---|---|---|
| 5,350,391 | 9/1994 | Iacovelli | 606/170 |
| 5,368,600 | 11/1994 | Failla et al. | 606/139 |
| 5,454,827 | 10/1995 | Aust et al. | 606/207 |

*Primary Examiner*—Michael Powell Buiz
*Assistant Examiner*—Vy Q. Bui
*Attorney, Agent, or Firm*—St. Onge Stewart Johnston & Reens LLC

[57] ABSTRACT

A medical handling device, in particular for endoscopic applications, has a distally arranged medical instrument, a proximally arranged handle which has a grip part that can be gripped with the hand, and further a shaft part arranged between instrument and handle. It is proposed that the grip part gripped by a human hand can pivot relative to the shaft part about both the volar flexion axis and the dorsal flexion axis of the wrist, with no change occurring thereby in the position of the shaft part.

13 Claims, 4 Drawing Sheets

VUMEDICAL HANDLING DEVICE IN PARTICULAR FOR ENDOSCOPIC APPLICATIONS

The present invention relates to a medical handling device, in particular for endoscopic applications, having a distally arranged medical instrument, having a proximally arranged handle which has a grip part that can be gripped with the hand, and having a shaft arranged between instrument and handle.

A medical handling device of this kind is known from PCT/DE95/01196.

In this handling device, the grip part is ergonomically shaped in such a way that it can be grasped essentially with one hand, at least between the ball of the thumb and the metacarpus or the inner finger bones, and can be held without the use of at least the outer and middle joints of the index finger and middle finger. For at least the index finger and middle finger, a separate actuation element is provided in each case, each of which is configured so that when it is actuated with the free fingertip of the associated finger, the other regions of the hand and fingers remain substantially in the gripping or holding position.

This handling device can certainly be held comfortably and firmly in the hand because of its ergonomic shape, and the actuation elements can be actuated with a finger; it is nevertheless disadvantageous that the position of the grip part relative to the shaft part is unchangeable.

For many operative techniques and also for many operators, it is uncomfortable or undesirable that despite the ergonomic shape of the grip part, the relative position between grip part and shaft is rigidly defined.

In most cases the operator's forearm extends in the longitudinal direction of the shaft; but the angular position of the hand and the bend of the wrist are then predetermined by the ergonomic configuration of the grip part.

If the operating placement or desired posture of the operator is then not suitable for the aforesaid position, uncomfortable angular positions of the wrist are necessary, and with long and difficult operations can lead to fatigue and pain in the wrist.

It is the object of the present invention to provide a remedy here, and to develop a medical handling device of the kind cited initially in such a way that any desired ergonomic positions of the wrist relative to the shaft part are possible.

This object is achieved by a medical handling device, comprising a shaft, a medical instrument disposed at a distal end of said shaft, a handle disposed at a proximal end of said shaft, said handle is provided with a grip part, said grip part is pivotally mounted to said shaft, and said grip part can pivot about two axes perpendicular one to another, wherein said grip, once gripped by a human hand, can pivot about both, the volar flexion axis of the wrist and the dorsal flexion axis of the wrist, with no change occurring thereby in the position of the shaft.

The two pivot axes about which the grip part can pivot relative to the shaft are located approximately in the natural flexion axes of the human wrist, i.e. on the one hand in the dorsal flexion axis, so that the grip part being gripped can be pivoted laterally relative to the shaft; and on the other hand about the volar flexion axis, so that the grip part can additionally be pivoted upward and downward relative to the shaft.

It is now therefore possible for the person who has grasped the grip part to perform natural pivot movements of the wrist with no need, for that purpose, to change the relative position of the forearm and shaft, so that, for example, the operator can bring his or her hand into a position that is comfortable for him or her, or simply into an ergonomically advisable position.

If it should be necessary because of operative techniques to bend the forearm in extreme fashion with respect to the shaft, said bending can be compensated for by pivoting the wrist in order to compensate for said extreme or uncomfortable bending, without moving the shaft during said pivoting movement. This is very important in the case of endoscopic, and in particular microendoscopic, operative procedures.

In an embodiment of the invention, the grip part is configured so that it can be grasped by the thumb and the inner surface of the hand.

The considerable advantage of this feature is that the grip part can be grasped, approximately like a rod, with the palm and the thumb, the other four fingers being unnecessary for this purpose. This type of grip already makes it possible to perform the pivot movements about both the dorsal and the volar flexion axes. The other four fingers are then therefore available for actuation of one or more actuation parts on the handle, for example to actuate an instrument that is configured as a grasping forceps with movable jaw parts. Prior to the actual actuation procedure, the operator can pivot the gripped grip part into a wrist position that is comfortable for him or her. This of course also opens up the possibility of providing several different actuation elements, for the respective actuation of which the wrist can be brought into an ergonomically favorable position.

In a further embodiment of the invention, the grip part is carried by a first lever which is pivot-mounted in articulated fashion on a second lever, the second lever being pivot-mounted in articulated fashion on the shaft, and the pivot axes of the levers coinciding approximately with the volar and the dorsal flexion axes of a human wrist grasping the grip part.

The advantage of this feature is that mechanically simple components are used to create design possibilities, on the one hand that of creating the pivot capabilities, and on the other hand that of bringing the actual grip part, by means of the levers, to the pertinent distance from the wrist. This also opens up the possibility, for example by means of adjustable levers, of creating the handle for persons with extremely small or extremely large hands, i.e. with a relatively large distance between the pivot point of the wrist and the grip recess on the inner hand surface. The levers moreover represent simple mechanical components which can be interconnected by means of corresponding simple hinge joints, which also meet the requirements for hygiene and for the sterilization of such devices.

In a further embodiment of the invention, a bent bracket, the bent portion of which extends approximately parallel to the longitudinal axis of the shaft, projects laterally at the proximal end of the shaft, and the second lever is attached in articulated fashion at the proximal end of the bent portion.

This physically simple configuration with the bent bracket makes possible a movement clearance for the two levers, so that these pivot movements at the proximal end of the shaft part can be performed unimpeded.

In a further embodiment of the invention, the second lever is configured as a laterally bent bracket at whose free end, approximately at the level of the longitudinal axis of the shaft, the first lever is pivot-mounted.

The advantage of this embodiment is that a centered position of the grip part is possible, in which the latter is located approximately in the central longitudinal axis of the shaft, and thus a starting position or neutral position is possible in which the forearm can extend approximately in the longitudinal axis of the shaft and the wrist is not bent either laterally or upward or downward. From this center position it is then possible to bring the wrist into the particular position that is ergonomically most favorable or comfortable without needing, for that purpose, to modify the relative position between forearm and shaft axis. In a further embodiment of the invention, the handle is in working engagement with the distally arranged medical instrument in such a way that the pivot movements of the handle about the volar and/or dorsal flexion axis are converted into corresponding pivot movements of the instrument.

The considerable advantage of this feature is that the pivot movements can now be actively converted, by the working engagement, into corresponding pivot movements of the instrument.

In this latter embodiment, the pivotability about the dorsal and volar flexion axes serves as an actual functional control movement of the medical instrument. This is referred to as an "active" or "functional" embodiment, as opposed to the aforementioned "passive" operational embodiment.

The working engagement makes it possible to transfer the pivot movements correspondingly, i.e. in the same direction, to the medical instrument at the distal end, so that the latter synchronously performs the same pivot movements as the wrist which has gripped the grip part. Thus for example, if the wrist is pivoted downward, the medical instrument at the distal end is also pivoted downward. Correspondingly, said medical instrument is pivoted upward if the wrist is pivoted upward. Simultaneously, and superimposed on said movements, the medical instrument at the distal end can also be pivoted left and right depending on whether the wrist is pivoted left or right. Because the fingers remain free, they can then be utilized to actuate the medical instrument, via existing actuation elements, in any desired pivoted position. If the medical instrument is, for example, configured as a cutter, it can, for example, be inserted into the body via an endoscope in a linear orientation with respect to the shaft; brought into an appropriate position by pivoting the handle; pivoted, for example, to the right and upward; and then, in this pivoted position, actuated for its actual function, for example by opening and closing the cutters by means of actuation elements actuated with the fingers. This therefore makes possible not only an ergonomically favorable hand position, but also controlled movement of the medical instrument, which synchronously follows the pivot movements of the hand about the dorsal or volar flexion axis of the wrist.

The medical instrument can also be or contain a high-frequency electrode of mono- or dipolar type and/or a camera. In the latter case, the operative field can be observed in all spatial directions by means of the camera.

The handle can also be decoupled from the shaft or the medical instrument in such a way that a telepresence technology can be applied.

In a further embodiment of the invention, the working engagement is accomplished via sheathed cables which transfer the pivot movement of the handle.

The advantage of this feature is that the pivot movement is transferred precisely from the handle to the medical instrument by means of mechanically simple and robust components.

In a further embodiment of the invention, gimbals, by means of which the pivot movement about the volar and/or dorsal flexion axis can be transferred to the instrument, are provided between the shaft and handle.

The dorsal and volar flexion axes are located perpendicular to one another, a configuration that is also present in gimbals, so that the pivot movement of the grip part can be transferred to the medical instrument by means of mechanically simple, robust, and accurately operating means. Provision can also be made for providing corresponding gimbals at the distal end, which are joined by means of corresponding cables or sheathed cables to the gimbals at the proximal end in order to transfer the pivot movements synchronously.

In a further embodiment, actuation means are provided for actuating the instrument. An actuation element of said actuation means is arranged so that it can be actuated by the fingers of the hand which are gripping the grip part.

For example, if a cutting or grasping movement is to be performed with the medical instrument, the actuation element can be actuated by the middle finger, which is movable in very flexible fashion with respect to various relative or pivoted positions of the wrist, so that all the functions of the medical instrument can be performed with one hand simultaneously and, in particular, in any pivoted position of the handle. This improves not only the functionality but also, because of the ergonomic wrist position, the operating reliability of the device.

In a further embodiment of the invention, the actuation element is joined by means of an actuation member to the instrument, and said actuating means can be actuated independently of the particular pivoted position of the handle.

This physical embodiment makes it possible, as mentioned above, independently yet simultaneously to effect pivoting and actually to operate the medical instrument.

In a further embodiment of the invention, the shaft is configured as a tubular shaft, and is configured in particular as the shaft that can be inserted into the conduit of an endoscopic instrument, in particular into a trocar sleeve. In this embodiment, the medical handling device can be used for the widely practiced endoscopic operative technique.

In a further embodiment of the invention, a locking system is provided by means of which the handle can be locked in any desired pivoted position of the grip part.

The advantage of this feature is that once a desired or favorable pivoted position has been reached, the handle can be immobilized in that pivoted position.

It is understood that the features mentioned above and those yet to be explained below can be used not only in the respective combinations indicated, but also in other combinations or in isolation, without leaving the context of the present invention.

The invention will be described and explained in more detail below, with reference to certain selected exemplary embodiments in conjunction with the attached drawings, in which.

Figure 1:
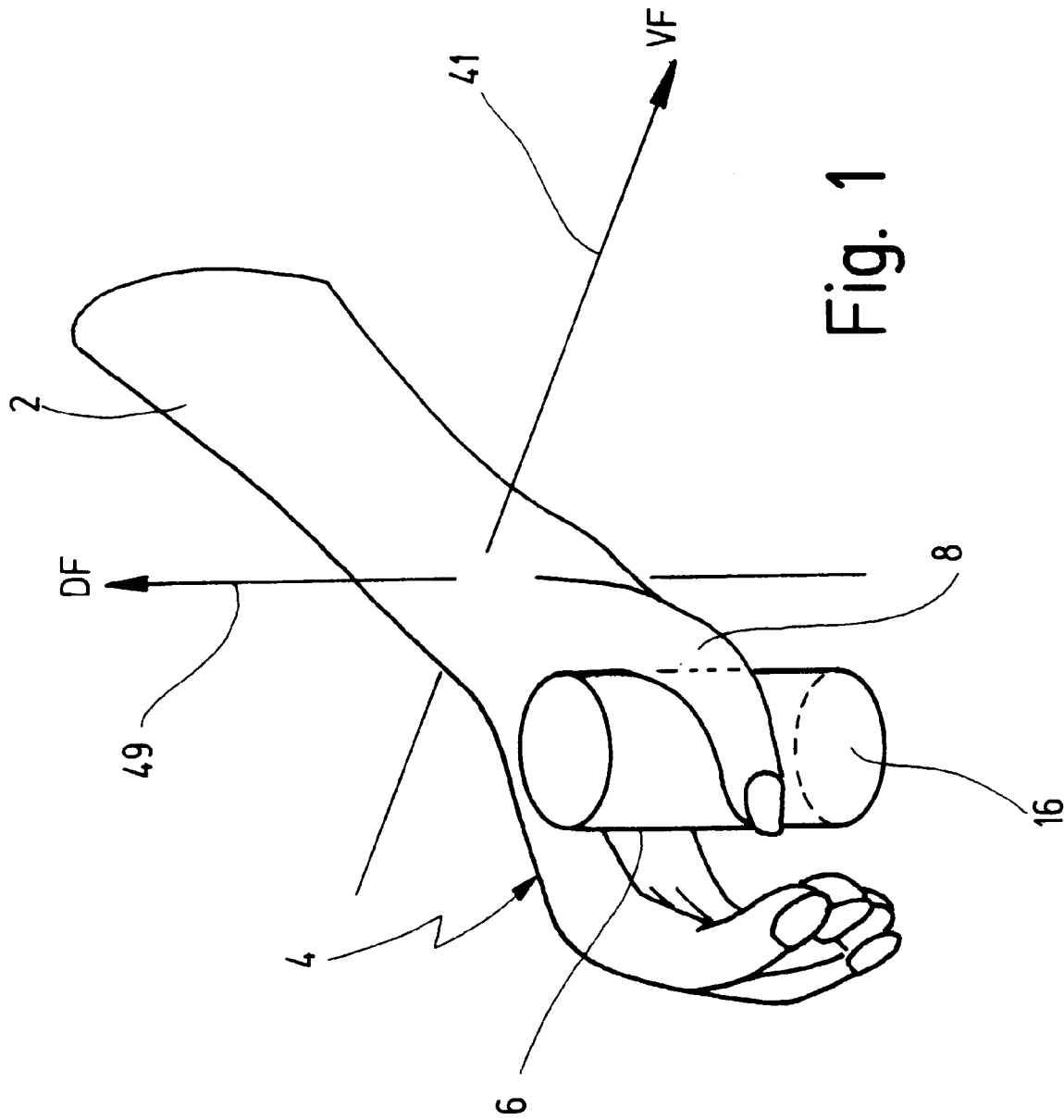
FIG. 1 shows, in highly schematic fashion, a human hand which has grasped a grip part of a medical handling device according to the invention.

FIG. 1 shows, in highly schematic fashion, a human right arm 2 and hand 4. An approximately cylindrical grip part 16 of a handling device according to the invention (to be described later in conjunction with FIGS. 2 to 4) is here grasped by the inner hand surface 6 and thumb 8. An axis labeled with reference character 41 corresponds to volar flexion axis VF of the human wrist. In pivoting about the volar flexion axis, hand 4 moves upward or downward.

Reference character 49 designates dorsal flexion axis DF of the human wrist. In pivoting about dorsal flexion axis DF, hand 4 moves to the left and right.

As is evident from FIG. 1, it is not necessary also to utilize the fingers in order to grasp grip part 16 securely; the pressure of the thumb is entirely sufficient for the purpose.

Figure 2:
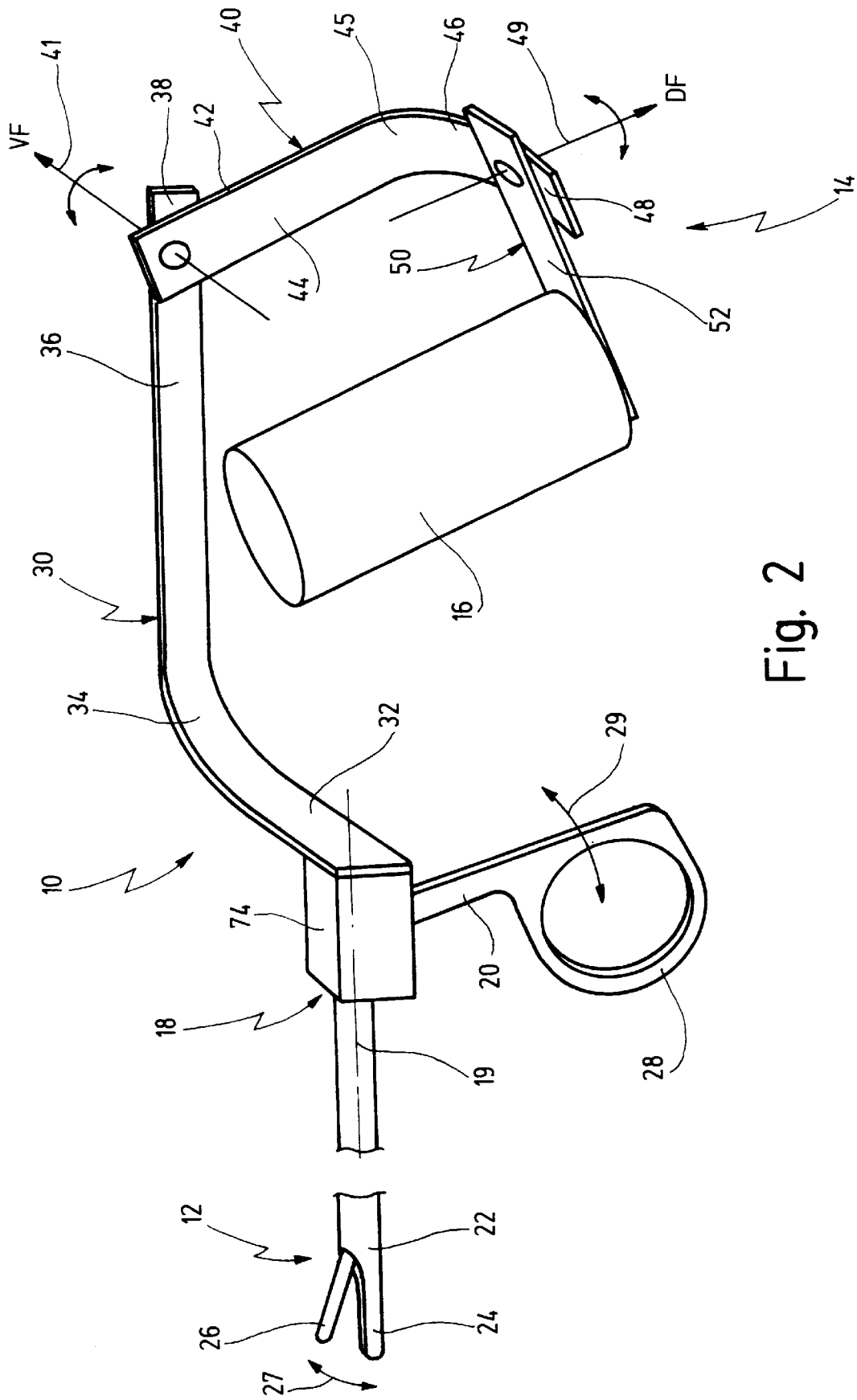
FIG. 2 shows, in highly schematic fashion, a first embodiment of a medical handling device.

In FIG. 2, a handling device in its entirety is designated, in highly schematic fashion, with the reference number 10.

Handling device 10 has at the distal end a medical instrument labeled in its entirety with the reference number 12.

Present at the proximate is a handle which is labeled in its entirety with the reference number 14 and has grip part 16 mentioned in FIG. 1.

Extending between medical instrument 12 and handle 14 is a shaft 18, which in the exemplified embodiment shown is configured as a tubular shaft whose longitudinal axis 19 corresponds to the bore axis of the tube. A housing 74, from which an actuation element 20 projects downward, is indicated schematically at the proximal end.

Medical instrument 12 is configured as a forceps 22 which has a fixed jaw part 24 and a moving jaw part 26. As indicated by a double arrow 29, actuation element 20 is received pivotably in housing 74, and is joined to movable jaw part 26 by means of an actuation member (not shown here). At the outer end, actuation element 20 is equipped with a finger ring 28 into which, for example, the middle finger of the hand shown in FIG. 1 can be inserted.

When actuation element 20 is pivoted back and forth in the direction of double arrow 29, movable jaw part 26 is pivoted in a direction described by double arrow 27.

A bent bracket 30 projects to the right (when viewed from proximal to distal) from housing 74.

Figure 3B:
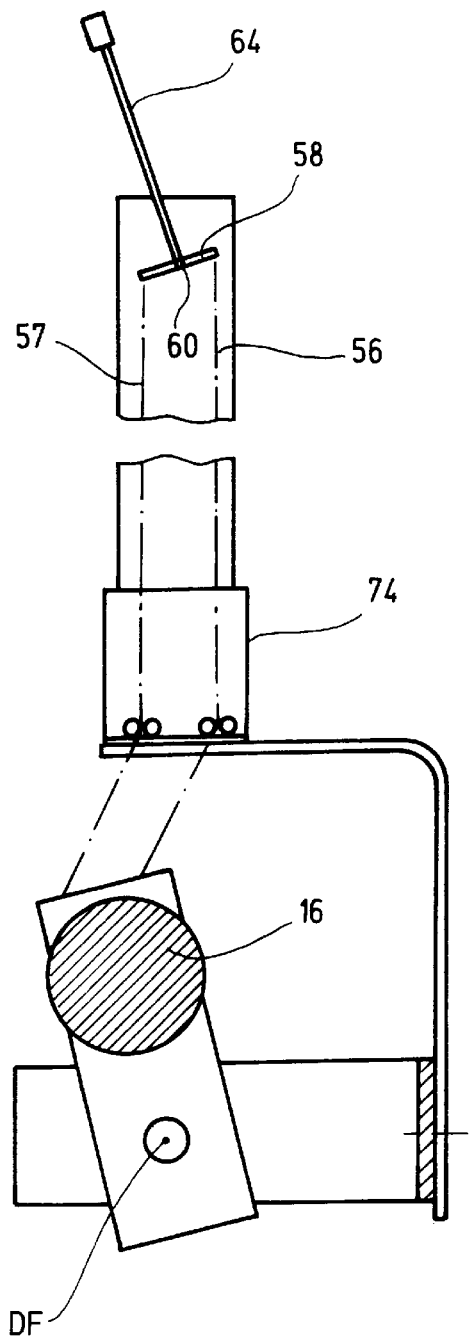
FIG. 3b shows a plan view corresponding to FIG. 3a but with the grip part in a pivoted position.
Figure 3A:
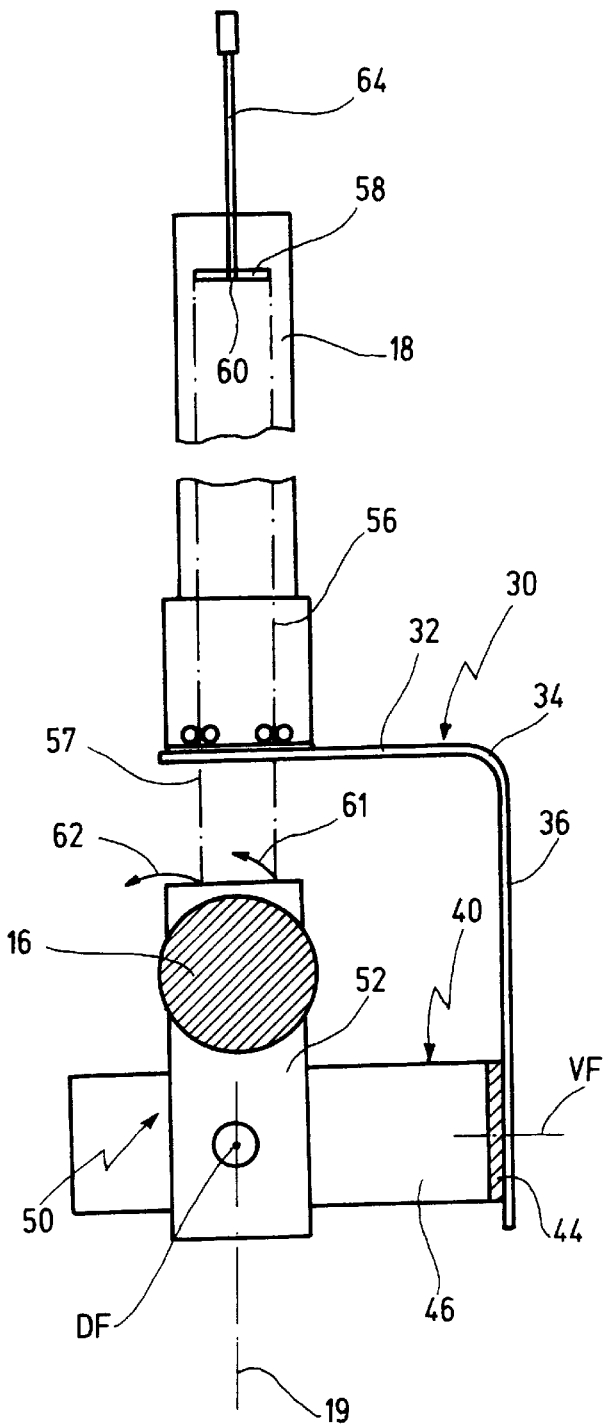
FIG. 3a shows a plan view of a medical handling device similar to the one shown in FIG. 2, but with functional connection between the handle and the distal end of the medical instrument.

Bent bracket 30 has an arm 32, extending at right angles to shaft axis 19, which continues via a curve 34 into a bent portion 36 which thus extends parallel to shaft axis 19 but offset laterally to the right, as is evident in particular from FIG. 3a.

A second lever 40 is attached in articulated fashion at proximal end 38 of bent portion 36.

The articulation axis of second lever 40 is selected so that it coincides approximately with volar flexion axis VF, 41 of a human wrist that is grasping grip part 16. Second lever 40 is configured as a bent bracket 42 which has an arm 44 one of whose ends is pivot-mounted on bent portion 36 and continues via a curve 45 into a bent portion 46. Bent portion 46 is thus oriented perpendicular to shaft axis 19, and extends approximately parallel to arm 32 of bent bracket 30, as is also evident particularly clearly from FIG. 3a.

First lever 50 is pivot-mounted on outer end 48 of bent portion 46 of second lever 40.

The articulation point is selected in this context so that its pivot axis corresponds approximately to dorsal flexion axis DF, 49 of a human wrist which is grasping grip part 16.

First lever 50 is configured as plate 52 which carries, at the end facing the shaft, the approximately cylindrical vertical grip part 16.

In the position shown in FIG. 2, grip part 16 is pivoted downward about the volar flexion axis.

If the person who has grasped grip part 16 has aligned his or her forearm so that it extends in the direction of shaft axis 19, the wrist is then bent slightly downward, which is ergonomically more favorable than the straight orientation. A wrist position of this kind may also be necessary during operations when the shaft is inserted into an endoscope and the operator simultaneously needs to look in the direction of shaft axis 19; this direction of view is impeded less by the downwardly bent wrist than by a wrist with a straight orientation.

By pivoting first lever 50, grip part 16 can also be pivoted to the left or right, and the wrist can correspondingly be pivoted about the dorsal flexion axis.

A locking system is provided (not shown) in order to immobilize grip part 16 in a particular position. The bolts of the articulations are designed as locking screws. The articulation points of the pivot axis can also be configured to be relatively tight, so that grip part 16 can still be pivoted, but then holds itself in position.

In the configuration shown in FIG. 2, handling device 10 is regarded as a "passive" functional element, i.e. the pivotability of handle 14 serves exclusively for ergonomically favorable positioning of the wrist, and the actual functionality of medical instrument 12 is accomplished exclusively via actuation element 20.

FIGS. 3a and 3b now depict an embodiment of the handling device of FIG. 2 in which pivoting of grip part 16 also has a functional effect on medical instrument 64 at the distal end.

In principle, the handling device shown in FIGS. 3a and 3b is approximately identical in design to the handling device shown in FIG. 2, so that for simplicity's sake the corresponding reference characters have also been retained.

It is evident from FIG. 3a that bent bracket 30, which projects to the right and on which second lever 40 is pivot-mounted pivotably about the volar flexion axis, is provided. First lever 50 is in turn pivot-mounted on second lever 40, pivotably about the dorsal flexion axis. It is evident from the representation in FIG. 3a that in the "neutral position" shown there, the central longitudinal axis of first lever 50 extends in the longitudinal direction of shaft axis 19. Grip part 16 carried by first lever 50 thus also extends centeredly with respect to shaft part 18. It is apparent from the representation in FIG. 3a that sufficient space is present around grip part 16 for a human hand to be placed around it.

Medical instrument 64 is arranged at the distal end pivotably about a pivot part 58; the pivot axis extends parallel to dorsal flexion axis DF and is located on shaft axis 19. The two lateral outer ends of pivot part 58 are connected by cables 56 and 57 to the distal edge of first lever 50, and extend approximately parallel.

When first lever 50 is then pivoted to the left about dorsal flexion axis DF into the position shown in FIG. 3b, the attachment points of cables 56 and 57 move as indicated in FIG. 3a by arrows 61 and 62, respectively. Arrow 61 indicates that the attachment point of cable 56 moves toward shaft axis 19 and simultaneously toward pivot part 58. Correspondingly, as indicated by arrow 62, the corresponding point of cable 57 moves away therefrom, so that pivot part 58 is pivoted synchronously with and in the same direction as the distal edge, so that the longitudinal axis of first lever 50 extends parallel to the longitudinal axis of instrument 64. In other words, the movement of the wrist to the left has been converted into a corresponding movement of instrument 64 to the left.

A corresponding situation exists when first lever 50 is pivoted to the right. It is of course possible, by means of a further cable pair rotated 90 degrees about shaft axis 19, correspondingly to convert the corresponding movement of grip part 16 upward or downward about the volar flexion axis.

If pivot part 58 is an inner ring of a gimbal mount, said ring is then suspended in a further ring which then effects the movement of the cables that are rotated 90 degrees.

Completely independently of this pivot movement, actuation of instrument 64 can be performed as before if the latter is configured, for example, as a forceps as described in conjunction with FIG. 2. In this case actuation element 20 is then connected by means of a flexible element to instrument 64 in such a way that the latter is guided exactly over pivot axis 60. Said guidance does not change the length of the corresponding actuation element which connects actuation element 20 and, for example, movable jaw part 26 when instrument 64 is simultaneously pivoted upward, downward, and/or to the left and right. It is evident therefrom that instrument 64 can be actuated in equally reliable fashion in any pivot position and independently thereof.

Figure 4:
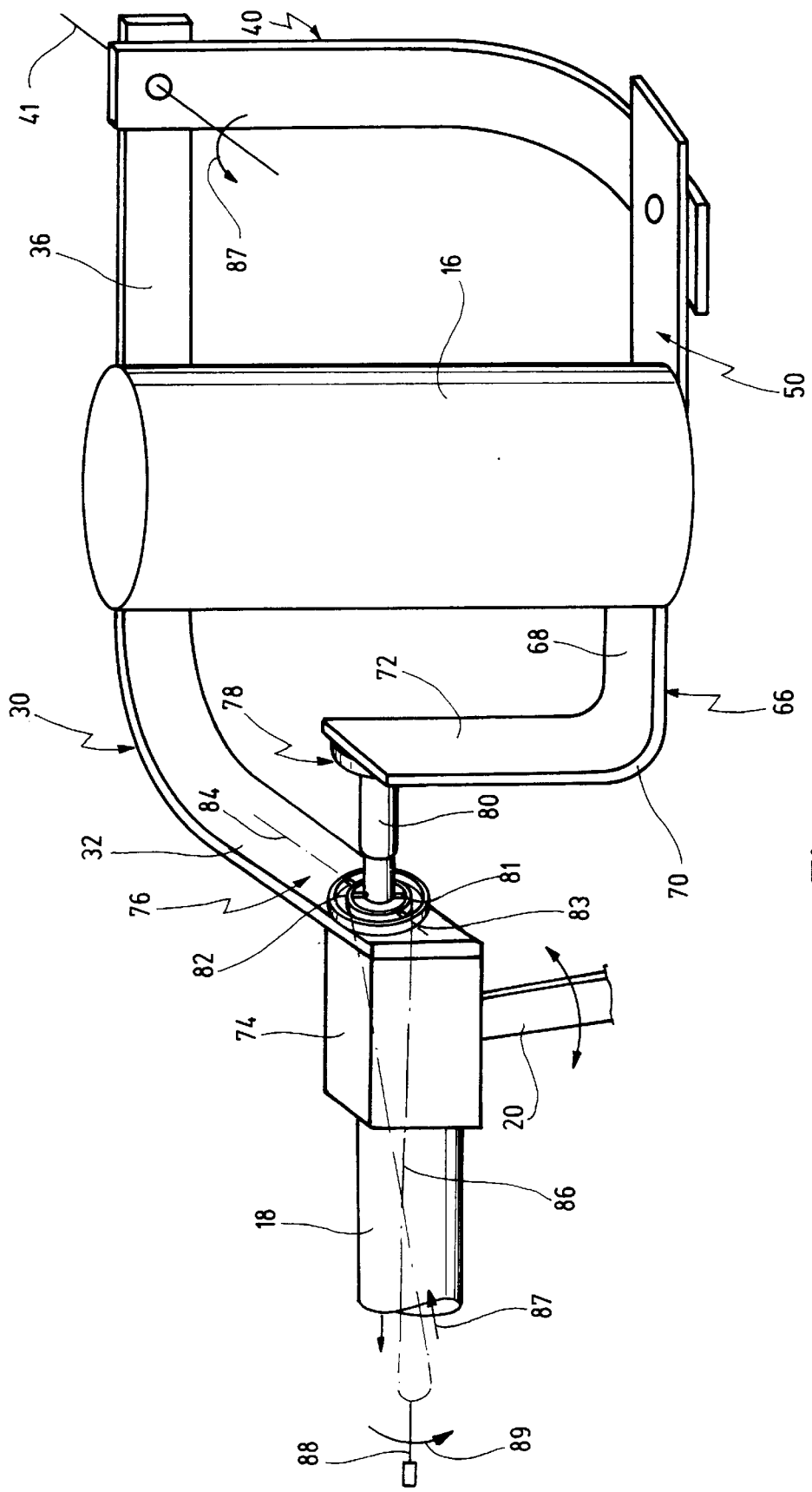
FIG. 4 shows, in highly schematic fashion, a partial perspective representation of a further exemplified embodiment of a medical handling device having functional coupling between the handle and medical instrument.

FIG. 4 shows a further embodiment of a handling device according to the invention which again is designed in fundamentally similar fashion to the handling devices described above. Here again, bent bracket 30 which carries second lever 40, the latter in turn carrying first lever 50, extends from shaft part 18.

Projecting from the distal end of first lever 50 is an upwardly bent bracket 66 which transitions from an arm 68, which still extends in the direction of first lever 50, via a curve 70 upward into a bent portion 72.

The upper end of bent portion 72 ends up at a distance behind the proximal end of housing 74.

Two gimbal mounts 76 and 78 are located opposite one another at the same height, and are interconnected via a telescoping rod 80.

Gimbal mount 76 at the proximal end of housing 74 has a first inner ring 82 which is immovably joined to one end of telescoping rod 80 via a vertical pin 81.

Inner ring 82 is pivotable in an outer ring 83 about an axis 84 pivoted 90 degrees with respect to pin 81. The opposing gimbal bearing 78 has the same configuration, but the attachment and pivotability of the inner and outer rings are rotated 90 degrees.

For example, if grip part 16 is pivoted downward, the end of telescoping rod 80 joined to gimbal mount 78 is lowered downward and inner ring 82 is thereby pivoted about axis 84; as a result, the upper (in FIG. 4) end emerges out of the ring plane of outer ring 83.

Said upper end of inner ring 82 is joined to a cable 86 that is guided, looped in figure-eight form, about a bearing (not shown in further detail here) of instrument 88.

When cable 86 is moved by ring 82 in the direction of arrow 87 in the course of the pivot motion described earlier, instrument 88 also moves downward as indicated by an arrow 89. Thus here again, transfer or conversion of the pivoting of grip part 16 in the same direction is ensured. The same applies for pivoting upward or to the left or right.

From any pivoted position and irrespective thereof, the instrument, for example when it is configured as a forceps, can then once again be actuated by pivoting actuation part 20.

A mechanical coupling via the sheathed cables or gimbal mounts has been described in each of the exemplified embodiments shown.

It is also possible to sense the pivot movements by means of sensors, and thereby initiate corresponding movements of the instrument.

It is, of course, also possible to integrate the pivot movements about the volar and dorsal flexion axes into a gimbal mount, i.e., for example, bent bracket 30 extends correspondingly on both sides of shaft part 18 and carries the first lever as described, or grip part 16 itself extends along a diameter of a gimbal-mounted ring.

We claim:

1. Medical handling device, comprising
   a shaft,
   a medical instrument disposed at a distal end of said shaft,
   a handle disposed at a proximal end of said shaft, said handle is provided with a grip part,
   said grip part is pivotally mounted to said shaft, and
   said grip part can pivot about two axes perpendicular one to another,
   wherein said grip, once gripped by a human hand, can pivot about both, the volar flexion axis of the wrist and the dorsal flexion axis of the wrist, with no change occurring thereby in the position of the shaft.

2. Medical handling device according to claim 1, wherein said grip part is configured in that it can be grasped by the thumb and the inner surface of the human hand.

3. Medical handling device according to claim 1, wherein said grip part is carried by a first lever which is pivotally mounted in an articulated fashion on a second lever, said second lever is pivotally mounted in an articulated fashion on the shaft,
   and wherein a pivot axis of the one of the two levers coinciding approximately with the volar axis of the human hand grasping the grip part and a pivot axis of the other one of the two levers coinciding approximately with the dorsal flexion axis of the human hand grasping the grip part.

4. Medical handling device according to claim 3, wherein a bent bracket is provided at said proximal end of said shaft, said bent bracket projects laterally from the proximal end of said shaft, a bent end section of said bent bracket extends approximately parallel to a longitudinal axis of said shaft, and said second lever is attached in an articulated fashion at a proximal end of said bent end section of said bent bracket.

5. Medical handling device according to claim 4, wherein said second lever is configured as a laterally bent bracket at whose free end, approximately at the level of a longitudinal axis of the shaft, the first lever is pivotally mounted.

6. Medical handling device according claim 1, wherein said handle is in working engagement with the medical instrument arranged at the distal end of said shaft, said working engagement is in that the pivot movements of the grip part about the volar and/or the dorsal flexion axis are converted into corresponding pivot movements of the instrument.

7. Medical handling device according to claim 6, wherein said working engagement is accomplished via sheathed cables which transfer a pivot movement of the handle to the instrument.

8. Medical handling device according to claim 7, wherein said working engagement is accomplished via gimbals provided between said proximal end of said shaft and said handle.

9. Medical handling device according claim 1, wherein actuation means are provided for actuating the instrument, said actuating means comprises an actuation member arranged in that it can be actuated by the fingers of the hand gripping the grip part.

10. Medical handling device according to claim 1, wherein said shaft is configured as a tubular shaft.

11. Medical handling device according to claim 1, wherein said shaft can be inserted into a conduit of an endoscopic instrument.

12. Medical handling device according to claim 11, wherein said endoscopic instrument, into which the shaft part can be inserted, is a trocar sleeve.

13. Medical handling device according to claim 1, wherein locking means are provided, by means of which locking means the handle can be locked in any desired pivoted position of the grip.

* * * * *

UNITED STATES PATENT AND TRADEMARK OFFICE
CERTIFICATE OF CORRECTION

PATENT NO. : 5,908,436
DATED : June 1, 1999
INVENTOR(S) : Alfred Cuschieri and Tim Frank It is certified that error appears in the above-indentified patent and that said Letters Patent is hereby corrected as shown below:

Column 1, title, "Vumedical" should read --Medical--.

Cover page, title, "Vumedical" should read --Medical--.

Signed and Sealed this

Twenty-second Day of May, 2001

Attest:

NICHOLAS P. GODICI

*Attesting Officer*　　　*Acting Director of the United States Patent and Trademark Office*